United States Patent [19]  [11] 4,374,382
Markowitz  [45] Feb. 15, 1983

[54] MARKER CHANNEL TELEMETRY SYSTEM FOR A MEDICAL DEVICE

[75] Inventor: Harold T. Markowitz, Anoka, Minn.

[73] Assignee: Medtronic, Inc., Minneapolis, Minn.

[21] Appl. No.: 225,561

[22] Filed: Jan. 16, 1981

[51] Int. Cl.³ .......................... A61N 1/30; A61B 5/00
[52] U.S. Cl. .......................... 340/870.01; 128/419 P; 128/696
[58] Field of Search ............... 128/696, 697, 903, 701, 128/260, 419 PT, 419 PS, 419 PG, 419 P; 340/870.01, 870.19, 870.21

[56] References Cited

U.S. PATENT DOCUMENTS 3,662,759  5/1972  Dabolt ............................ 128/419 P
3,920,005  11/1975 Gombrich et al. ........... 128/419 PT
4,156,430  5/1979  King et al. ..................... 128/419 PT
4,281,664  8/1981  Duggan ......................... 128/419 PT Primary Examiner—Thomas A. Robinson
Attorney, Agent, or Firm—Robert C. Beck; John L. Rooney; Joseph F. Breimayer

[57] ABSTRACT

A marker channel telemetry system for use with a pacemaker or other medical device for transmitting event identifying codes to a remote receiver to indicate the occurrence of specific events such as sensed and paced events in a dual chamber pacemaker. The structure of the system includes latches to store event information and for forming the marker codes. The system also includes a serial telemetry transmitter for transmitting the data to the remote receiver.

6 Claims, 4 Drawing Figures

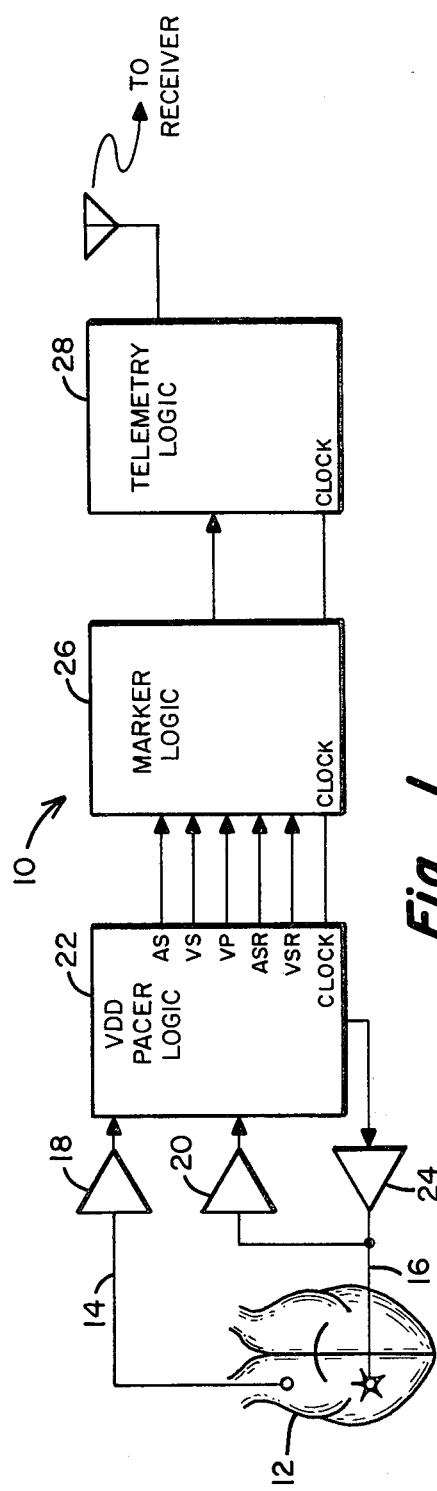
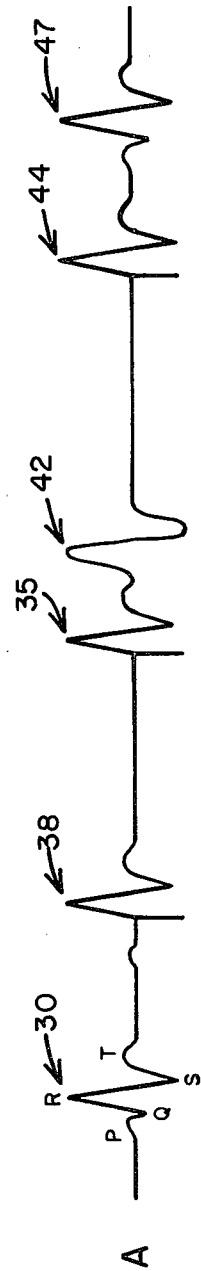
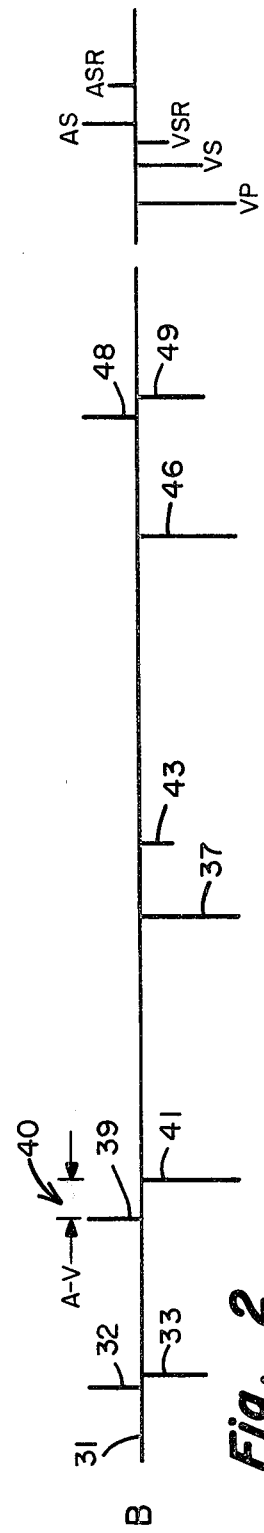
Fig. 1
Fig. 2

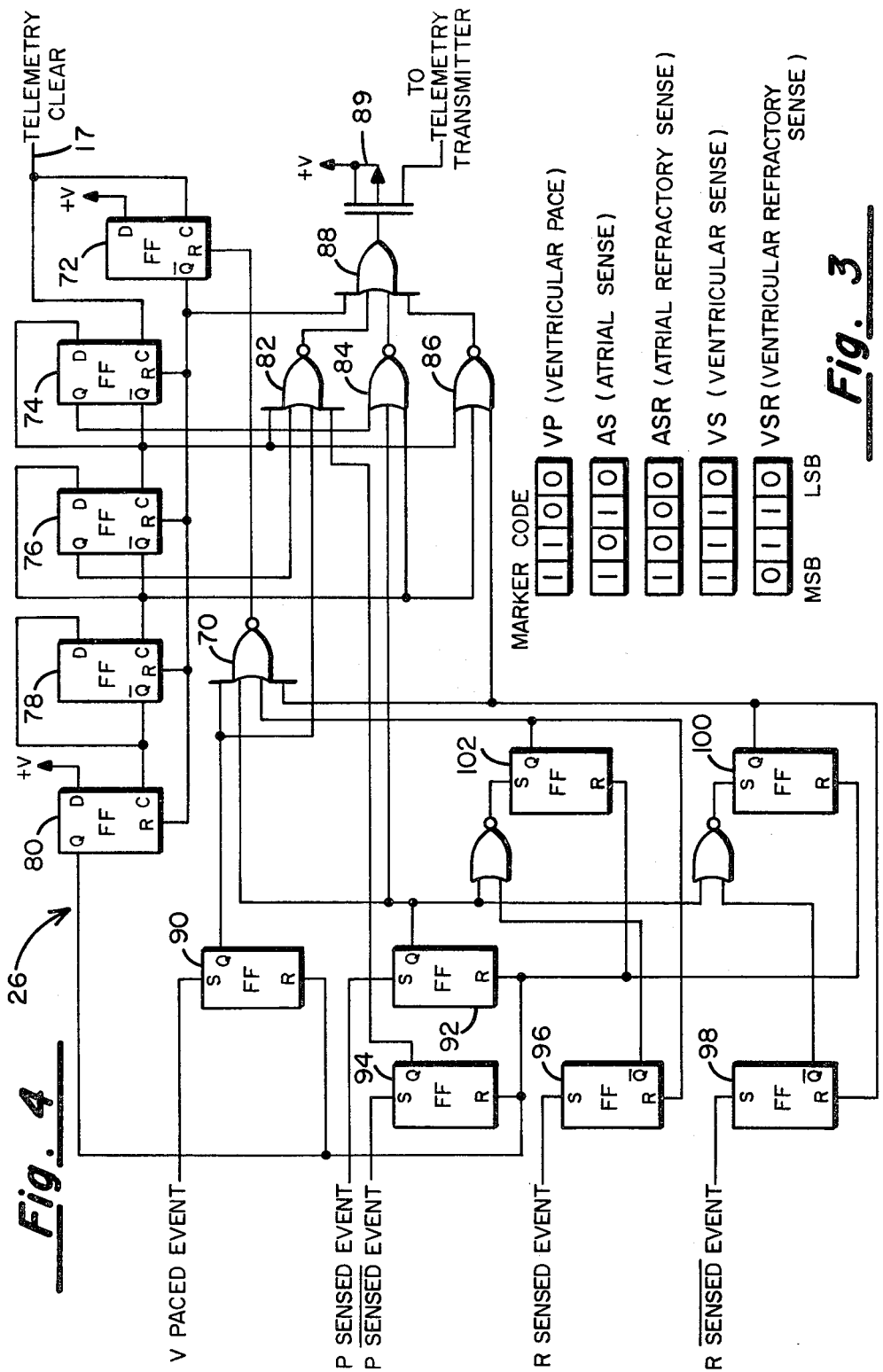

MARKER CHANNEL TELEMETRY SYSTEM FOR A MEDICAL DEVICE

BACKGROUND OF THE INVENTION

1. Field of the Invention

This invention relates to a telemetry system for use in an implantable medical device, such as a pacemaker. More specifically, it relates to a telemetry system for use with a dual-chamber pacemaker for transmitting an indication of when various sensed or paced events have occurred. The telemetered data is received and decoded at a remote receiver where it may be displayed and used for diagnostic purposes.

2. Description of the Prior Art

Cardiac pacemakers which supply electrical stimulation to the heart in the absence of natural occurring heartbeats are well known. Traditionally, such pacemakers were manufactured utilizing discrete analog circuitry. More recently, pacemakers have been designed with digital circuitry of great complexity. This additional capability has been used to expand the operating modalities of the pacemaker to encompass both chambers of the heart and has also been used to add desirable features such as programmability and telemetry capabilities. These modern pacemakers interact with the heart in a complex fashion which complicates follow-up care if traditional pacemaker diagnostic techniques are used.

It has proved desirable to check the pacemaker patient on a routine basis to verify the proper operation of the pacemaker. Traditionally, this task has been accomplished with the aid of an electrocardiogram (ECG) which records the electrical activity detected on the skin surface of the patient. This ECG will display the physiological waveform of the heart as a complex periodic waveform with P, Q, R, S and T portions. This ECG will also display the pacemaker stimulating pulse as a narrow pacemaker artifact on the same ECG trace. By noting the relationship between the pacemaker artifact and various elements of the physiological waveform, the physician can analyze the operating characteristics of the pacemaker to verify its proper and safe performance. However, modern dual-chamber pacemakers have responses which may be difficult to diagnose based solely on the electrocardiogram. Consequently, there is a need to provide additional information to the attending physician to simplify the analysis of pacemaker operation.

One prior art technique which is related to the problem stated above is taught by Dabolt in U.S. Pat. No. 3,662,759. In Dabolt a narrow sub-threshold pulse is applied to the heart via the lead system each time the demand pacemaker escape interval is reset by sensed spontaneous activity. This sub-threshold pulse is insufficient to stimulate the heart; however, its steep rise time generates sufficient radio frequency harmonics to be detected by a conventional radio receiver. In operation a radio "click" is produced each time a naturally occurring R-wave is detected and used by the pacemaker circuitry to reset the escape interval of the pacemaker. The objective of Dabolt is to verify proper sensing by the pacemaker of the naturally occurring heartbeat. Although Dabolt's system provides a convenient method of producing a remote indication of a sensed event with a minimum of equipment, no permanent record is produced by this technique nor is the system applicable to the analysis of more complex dual-chamber pacemakers.

SUMMARY OF THE INVENTION

By way of contrast, the present invention provides a useful remote indication of when pacemaker sensed, paced and other events have occurred. This information is encoded and transmitted to a remote receiver where it may be decoded and displayed on a conventional ECG machine in conjunction with a recording of the physiological waveform as an aid to pacemaker diagnostics.

The structure of the present invention includes a telemetry system for transmitting information from the pacemaker to a remote receiver. The telemetry information is developed by a digital encoding system which produces several multi-bit digital words used as event identifying markers. In operation a sensed or paced event will initiate the formation and transmission of the appropriate marker code to the remote receiver.

The telemetry signal is received and decoded by the receiver and displayed on an ECG machine simultaneously with the recorded physiological waveform thus indicating the type of event which has occurred and its temporal relation to the physiologic waveform.

BRIEF DESCRIPTION OF THE DRAWINGS

FIG. 1 is a block diagram showing the functional relationship between the elements of the invention;

FIG. 2 is the data display scheme used in practicing the invention; and

FIG. 3 is the data encoding scheme used for practicing the invention;

FIG. 4 is a schematic representation of one method of implementing the invention.

DETAILED DESCRIPTION OF THE PREFERRED EMBODIMENT

In FIG. 1 a dual-chamber pacemaker 10 is shown connected to a heart 12 through a lead system having both atrial, 14, and ventricular, 16, conductors. These conductors connect with atrial, 18, and ventricular, 20, sense amplifiers which produce output signals in response to detected atrial and ventricular depolarizations. The sense amplifiers are connected to the pacer logic 22, which produces stimulating pulses applied to a ventricle through an output buffer 24 in accordance with a dual-chamber pacing modality. Signals are developed within the pacer logic which correspond to various events which are useful in the analysis of surface electrocardiograms. These signals are labeled AS for an event sensed by the atrial sense amplifier 18, VS for events detected by a ventricular sense amplifier 20, VP for the application of a ventricular stimulating pulse through output circuit 24, and ASR for an atrial event detected within atrial refractory period and VSR for a ventricular event detected within the ventricular refractory period. These latter signals correspond to detected cardiac depolarizations which are sensed by the pacemaker but which are not normally used to control the pacing therapy by pacer logic 22. Each of these signals is connected to an appropriate signal path to the marker channel logic 26, which includes these events and initiates the operation of telemetry transmitter 28 which transmits these signals to an appropriate receiver which is not shown.

This receiver accepts the telemetry signal and decodes it in a form suitable for display on a multi-channel electrocardiograph. Each of the marker channel events is uniquely displayed on one channel of the multi-channel recorder in conjunction with the normal surface electrocardiograms. The simultaneous display of the marker channel data in synchrony with the cardiac activity recorded from the surface of the patient permits the unambiguous analysis of the electrocardiogram and, in particular, permits the attending physician to quickly discern the interaction between the pacemaker and the heart.

Although the following description relates to an atrial synchronized ventricular inhibited pacer, or VDD mode pacemaker it should be understood that the concepts taught are applicable to all modes of pacing.

The VDD form of pacer provides stimulating pulses to the ventricle in the absence of naturally occurring cardiac depolarizations and closely mimics the operation of the normal heart by synchronizing on sensed atrial depolarizations. In operation, the detected atrial activity triggers a stimulating pulse to the ventricle after an appropriate atrial-ventricular delay unless the ventricular sense amplifier detects a ventricular beat within a preset A-V time period.

An example of the use of the marker channel data is shown in FIG. 2 wherein the upper waveform A is a surface electrocardiogram. The first complex 30 on this waveform is a normal beat having P, Q, R, S and T portions labeled on the diagram. The second waveform B shows one possible representation of the marker channel data on an analog electrocardiograph display. In this format, the amplitude of excursions above and below the isoelectric line 31 are used to indicate which of the various marked events have occurred. In this format, the excursion 32 above the isoelectric line appearing beneath the P-wave portion of the electrocardiogram complex 30 indicates that the pacemaker atrial sense amplifier 18 has detected that P-wave. Likewise, the excursion 33 below the isoelectric line occurring the synchrony with the R-wave indicates that the pacer has detected the R-wave and has telemetered a ventricular sensed event signal.

If the ventricular rate drops below the preset minimum rate, the pacemaker will operate in the demand mode stimulating the ventricle. This is shown in complex 35 where the absence of a detected P-wave has resulted in a ventricular paced event, shown by ventricular pace marker 37. If the interval between successive ventricular complexes is shorter than the programmed escape interval of the pacemaker, then no ventricular stimulating events will be produced and proper operation of the pacemaker may be verified by the appearance of these ventricular sense markers.

In a similar fashion, a conduction disturbance which prevents a naturally occurring atrial depolarization from stimulating the ventricles will be identified by electrocardiogram and marker channel data shown in complex 38. In this instance, the detected atrial depolarization shown by marker channel deflection 39 has not been followed by a spontaneous or conducted R-wave within a preset A-V delay interval 40 and has resulted in a ventricular stimulating pulse 41.

Additional events which may be displayed by the marker channel include premature beats such as ventricular premature beat 42, which occurs during a refractory period and is indicated by ventricular sense refractory marker 43 on the marker channel. Complex 44 is similar to complex 35 in that it resulted from a low rate escape of the pacer as indicated by ventricular pace marker 46. Complex 47 is similar to complex 30 in that it is a normally conducted beat which is indicated by atrial sense marker 48 and ventricular sense marker 49.

The codes which result in the display of FIG. 2 are developed by marker channel logic 26 shown in FIG. 1 interfaced to the remaining pacemaker logic 22 through a number of interconnects. Appropriate logic levels are developed within the pacemaker logic 22 and delivered to the marker channel logic 26 via these interconnections when the specified events occur. The marker channel logic 26 then develops a suitable code to identify which of a number of events has occurred and relays this data in a serial format to the telemetry transmitter 28. It is desirable to clock the data in synchrony with the telemetry output rate. The use of a telemetry generated clock signal for synchronizing data is further discussed in commonly assigned, copending Application Ser. No. 194,807 filed Oct. 7, 1980, which is incorporated by reference herein.

FIG. 4 shows a logic implementation which can be used to form the marker code and serialize these codes in synchrony with the telemetry system. Operation of the circuitry is initiated by the occurrence of a logic level signal on any of the event interconnect lines. The interconnect lines at the left of FIG. 4 do not correspond directly to the events listed in FIGS. 1 and 3. A ventricular pace event VP is signalled by a logic 1 on the upper line labelled V PACED EVENT. Similarly a ventricular sense event VS and a ventricular refractory sense event VSR are signalled by a logic 1 on the lines labelled R SENSED EVENT and R SENSED EVENT, respectively. The atrial sense event AS is signalled by a logic 1 on the P SENSED EVENT line and a simultaneous logic 0 on the P SENSED EVENT line and the atrial refractory sense event ASR is signalled by a logic 1 on both the P SENSED EVENT and P SENSED EVENT lines. A logic 1 on any of the event interconnects causes one of the flip-flops 90-98 (or both flip-flops 92 and 94 in the case of an ASR event) to be set. Flip-flop 100 or 102 is set by a VSR or VS event if flip-flop 92 is cleared or not set as described later. The setting of one of the flip-flops 90, 92, 100, 102 indicating an event to be telemetered provides a 1 input to NOR gate 70, causing the output of NOR gate 70 to go low and removing a reset signal from D-type flip-flop 72. As a consequence, the next high transition of the telemetry clock at telemetry clock input 17 will force the Q output of flip-flop 72 to the logic zero condition removing the RESET signal from the counter chain formed by flip-flops 74, 76, 78 and 80. During this clock cycle flip-flops 74-80 remain reset and each NOR gate 82, 84, 86 receives a logic 1 input from the Q output of flip-flop 74 and/or flip-flop 76. This results in the transmission of a logic 0 through OR gate 88 and P-channel FET buffer 89 to the telemetry transmitter. The collection of flip-flops 74-80 forms a binary counter producing a sequence of output states which cause the NOR gates 82, 84, or 86 to go high to synchrony with the following first, second and third counts of the counter, respectively if at that time they are receiving low inputs from the flip-flops 90-102 connected to their other inputs. The sequence of output states are applied to OR gate 88 which has an output state which goes high when any of the NOR gates 82-86 outputs go high. Thus the second transmitted bit is 0 when either flip-flop 90 or 94 is set (VP or ASR); the third bit is 0 when flip-flop 92 is set (AS or ASR); and the fourth bit is 0 when flip-flop 100 is set (VSR). The codes shown in FIG. 3 are in fact repeated on counts 4-7 of the counter and on count 8 flip-flop 80 is set, resetting flip-flops 90, 92, 94, 100 and 102. Having thus described the generation of the marker codes when appropriate logic level signals are applied to the inputs of NOR gate 70, we proceed with a description of the remaining logic shown in FIG. 4.

The numerous flip-flops which interface the event interconnects to NOR gate 70 cooperate to prioritize the transmission of marker codes. For example, if two events occur simultaneously, it may be more desirable from a diagnostic viewpoint to telemeter the more significant events and ignore the less significant event.

It is also important to latch the occurrence of an event, since an event may occur before the transmission of a preceding marker code has been completed. The flip-flops shown in FIG. 4 as 90-102 cooperate to latch the occurrence of an event communicated from pacemaker logic 22 and to prioritize events which occur within a rapid sequence.

For example, if a VS or VSR event occurs while an AS or ASR event is being transmitted, flip-flop 96 or 98 is set to latch the event but no signal passes through the NOR gates to set flip-flop 102 or 100 because flip-flop 92 is set. When flip-flop 92 is cleared after transmitting the atrial event code, flip-flop 100 or 102 is set to initiate the transmission of the latched ventricular event code.

In a further embodiment of the invention the pacemaker may be arranged to sense the pace both the atrium and ventricles of the heart. The marker logic 26 may be expanded to include additional codes to mark the occurrence of atrial paced events.

Although the preferred embodiment depicts the use of pen excursions by an ECG recorder to show the transmitted events, it will be understood that the encoded and transmitted signals may be received and recorded or displayed by differing means and formats and can be used by external equipment for automated analysis including telephone follow-up. In addition to the pacemaker embodiment described, it will be further understood that the invention may find utility in other implantable devices.

I claim:

1. An implantable medical device of the type having means for detecting physiological events and having means for stimulating physiological activity and having a telemetry system for non-invasive communication with a remote receiver, said telemetry system comprising means responsive to the detection of physiological events for producing a sensed event signal, latch means responsive to said sensed event signal for storing a signal indicating the occurrence of said sensed event, means responsive to the stimulation of physiological activity for producing a stimulated event signal, latch means responsive to said stimulated event signal for storing a signal indicating the occurrence of said stimulated event, encoding means for producing event identifying codes each representative of a said stored signal, and means for serially transmitting said event identifying codes to said remote receiver.

2. A device as claimed in claim 1 comprising a pacemaker having means for detecting cardiac electrical activity and means for stimulating the heart.

3. A device as claimed in claim 2 comprising an atrial sense amplifier for detecting physiological activity originating in the atrium, a ventricular sense amplifier for detecting physiological activity occurring in the ventricle and a ventricular stimulation circuit for producing a stimulation pulse to the ventricle, said detection responsive means comprising means responsive to the atrial sense amplifier for producing an atrial sense signal, and means responsive to the ventricular sense amplifier for producing a ventricular sense signal; and said stimulation responsive means comprising means responsive to the stimulation circuit for producing a stimulation event signal.

4. A device as claimed in claim 3 comprising an atrial stimulation circuit for producing a stimulation pulse to the atrium, and wherein said stimulation responsive means further comprises means responsive to the atrial stimulation circuit for producing an atrial stimulation event signal.

5. A device as claimed in claim 1 wherein said transmitting means further includes a clock output at the transmitted bit rate, said clock output being supplied to the encoding means for serializing said codes.

6. A device as claimed in claim 1 wherein said encoding means comprises a counter having outputs coupled to a plurality of gates, whereby to enable the gates on separate counts of the counter, the latch means being coupled to the gates whereby codes representative of the stored signals are supplied by the gates as the counter counts.

* * * * *

UNITED STATES PATENT AND TRADEMARK OFFICE
CERTIFICATE OF CORRECTION

PATENT NO. : 4,374,382
DATED : February 15, 1983
INVENTOR(S) : Harold T. Markowitz It is certified that error appears in the above-identified patent and that said Letters Patent is hereby corrected as shown below:

Column 3, line 38, "the" (third occurrence) should read -- in --;

Column 4, line 48, "Q" should read -- $\bar{Q}$ --;
          line 52, "Q" should read -- $\bar{Q}$ --;
Column 5, line 29, the first "the" should be -- and --;

Signed and Sealed this

Second Day of August 1983

[SEAL]

Attest:

GERALD J. MOSSINGHOFF

Attesting Officer    Commissioner of Patents and Trademarks